(12) United States Patent
Förster (10) Patent No.: US 7,255,557 B2
(45) Date of Patent: Aug. 14, 2007

(54) SELF-LIGATING BRACKET FOR USE IN ORTHODONTICS

(76) Inventor: Rolf Förster, Vogesenallee 58, D-75173 Pforzheim (DE)

( * ) Notice: Subject to any disclaimer, the term of this patent is extended or adjusted under 35 U.S.C. 154(b) by 0 days.

(21) Appl. No.: 11/281,988

(22) Filed: Nov. 17, 2005

(65) Prior Publication Data

US 2006/0110699 A1    May 25, 2006

(30) Foreign Application Priority Data

Nov. 18, 2004  (DE) .................... 10 2004 056 167

(51) Int. Cl.
*A61C 3/00* (2006.01)
(52) U.S. Cl. ................................................. 433/11
(58) Field of Classification Search ............. 433/10, 433/11, 13
See application file for complete search history.

(56) References Cited

U.S. PATENT DOCUMENTS

| 4,799,882 | A | * | 1/1989 | Kesling | ............ | 433/8 |
| 5,470,228 | A | * | 11/1995 | Franseen et al. | ................ | 433/8 |
| 5,586,882 | A | * | 12/1996 | Hanson | .............. | 433/13 |
| 5,906,486 | A |  | 5/1999 | Hanson |  |  |
| 2001/0005574 | A1 | * | 6/2001 | Manemann et al. | .......... | 433/11 |

FOREIGN PATENT DOCUMENTS

WO    WO 96/09015    9/1995

* cited by examiner

*Primary Examiner*—Cary E. O'Connor (57) ABSTRACT

The invention describes is a self-ligating bracket for use in orthodontics having a base (1); a support (4) arranged on the base (1); an occlusal wall (6) with at least one occlusal ligature wing (9) extending from the support (4); a gingival wall (5) with at least one gingival ligature wing (8) extending from the support (4); a slot (7) separating the occlusal wall (6) and the gingival wall (5) one from the other and extending continuously in the mesial-to-distal direction; a second slot (18) which extends continuously through the support (4) in the gingival-to-occlusal direction, and which is limited by a lingual surface (19) and by a labial surface (6a); and a resilient clip (25) having a labial leg (27) and a lingual leg (26) that are connected one to the other by an occlusal section (28); the lingual leg (26) being received in the second slot (18) and being arranged for displacement in the slot in the gingival-to-occlusal direction between a closed position in which the labial leg (27) extends into a recess (24) in the gingival wall (5) and an open position of the clip (25) in which the tip of the labial leg (27) rests on the occlusal wall (6). A tongue (30), directed toward the occlusal wall (6), is cut out from the lingual leg (26) of the clip (25) and is bent off in the labial direction so that an acute angle is enclosed between the tongue and the lingual leg (26) of the clip (25).

36 Claims, 7 Drawing Sheets

SELF-LIGATING BRACKET FOR USE IN ORTHODONTICS

BACKGROUND OF THE INVENTION

1. Field of the Invention

The present invention related to a self-ligating bracket for use in orthodontics.

2. Description of Related Art

A bracket of this kind has been known from U.S. Pat. No. 5,906,486. The known bracket comprises a base the bottom of which is prepared for being glued onto a tooth. The base carries a support which has a surface area generally smaller than the base. An occlusal wall and a gingival wall extending from the support include between them a groove which is open in the labial direction and which extends continuously from the mesial to the distal end, separating the occlusal wall and the gingival wall one from the other. In German technical language, just as in the English language, the groove is also described as "slot". It serves to receive an arch wire which usually runs through a succession of brackets mounted on a series of neighboring teeth. By drawing or twisting the wire a pre-stress can be produced in the wire which will be transmitted by the arch wire to the brackets, and from the latter to one or more teeth for the purpose of modifying the orientation of the teeth.

The occlusal wall and the gingival wall of the known bracket are each provided with one or two ligature wings on which ligature wires can be mounted.

In order to secure the position of the arch wire in the slot of the bracket, the known bracket is provided with a resilient clip comprising a labial leg and a lingual leg that are connected one with the other by a section arranged on the occlusal side. The clip is captivated on the bracket. The bracket is provided for this purpose with a slot which extends continuously through the support, from the occlusal to the gingival end, and which is defined by a wide lingual surface, a wide labial surface, and two narrow mesial and distal surfaces extending at a right angle relative to the first-mentioned surfaces. The lingual leg of the clip is received in that slot. The clip can be displaced between a closed position in which the labial leg extends into a recess in the gingival wall of the bracket and an open position in which the tip of the labial leg rests on the occlusal wall. In the open position, an arch wire can be fitted in the slot or can be removed from the slot. In the closed position, the labial leg of the clip closes the slot in the labial direction and is in resilient contact with the arch wire in order to press it down toward the bottom of the groove. In the event the arch wire exerts upon the labial leg of the clip a force that exceeds the restoring force of the clip, the recess in the gingival wall is limited by a labial stop which will be contacted by the labial leg of the clip when a sufficiently high force is exerted on the labial leg by the arch wire. Further, the stop in the gingival wall of the bracket limits the maximum dimension of the arch wire in the lingual-to-labial direction. In the closed position, the clip is held by the fact that the labial leg, when being displaced toward the closed position, will come into resilient contact with the occlusal wall, and can be transferred from its closed position to its open position only by bending it up elastically. In the open position, the clip of the known bracket can be held by an arrangement where the tip of the labial leg of the clip springs resiliently into a recess provided on the labial end of the occlusal wall.

For moving the clip from its closed position to its open position, the labial leg of the clip of the known bracket is provided with a hole that can be engaged by a pin. The pin can be used as a lever by means of which the clip can be moved from its closed position to its open position. That hole is connected with disadvantages. On the one hand, it weakens the clip. This disadvantage cannot be remedied by an increase in size of the clip because there exists a simultaneous demand that the bracket should be as small as possible. On the other hand, food particles may easily get into the space between the clip and the occlusal wall, through the hole in the clip, and may even be compacted by the chewing process. The food particles practically cannot be removed by usual tooth-cleaning methods, which is detrimental in terms of oral hygiene.

In order to prevent the clip from getting lost during transfer from the closed position to the open position, the tip of the lingual leg of the clip, being located outside of the slot, is provided with an embossed mark that will fit through the slot in which the lingual leg of the clip is received only if it is deformed elastically. The force required for sliding the embossed tip of the lingual leg of the clip through the slot may, however, very well be applied when transferring the clip to its open position so that there actually exists a risk of the clip getting lost or of the patient swallowing it.

Now, it is the object of the present invention to open up a way how the risk of the clip getting lost unintentionally can be reduced or avoided without much expense.

This object is achieved by a the inventive bracket.

The self-ligating bracket for use in orthodontics according to the invention comprises a base;

a support arranged on the base;

an occlusal wall with at least one occlusal ligature wing extending from the support;

a gingival wall with at least one gingival ligature wing extending from the support;

a first slot separating the occlusal wall and the gingival wall one from the other and extending continuously in the mesial-to-distal direction;

a second slot which extends continuously through the support in the gingival-to-occlusal direction, and which is limited by a lingual surface and by a labial surface; and a resilient clip having a labial leg and a lingual leg that are connected one to the other by an occlusal section;

the lingual leg being received in the slot and being arranged for displacement in the slot in the gingival-to-occlusal direction between a closed position in which the labial leg extends into a recess in the gingival wall and an open position of the clip in which the tip of the labial leg rests on the occlusal wall.

A tongue directed toward the occlusal wall of the bracket is cut out from the lingual leg of the clip and is bent off in the labial direction so that an acute angle is enclosed between the tongue and the lingual leg of the clip.

Such a tongue protects the clip from getting lost during transfer to its open position because, being directed toward the occlusal wall, the tongue will hit against the occlusal wall and be blocked when an attempt is made to move the clip beyond its open position during transfer to its open position from its closed position. Moving the lingual leg of the clip completely out of the second slot, thereby fully detaching the clip from the bracket, will be possible only by pushing the tongue back into the recess in the lingual leg of the clip and simultaneously pressing on the gingival end of the that leg of the clip, or pulling at the occlusal section of the clip. This cannot happen unintentionally. For pressing down the tongue, a tool, for example a pin or a scaler, must be inserted into the second slot from the labial direction. When sliding the clip onto the bracket the tongue will not be felt as an obstacle because it is introduced into the second slot with that end first which foots on the clip, being thus pushed into the recess in the lingual leg of the clip automatically. Consequently, the lingual leg of the clip can be introduced into the second slot of the bracket even more easily than the embossed lingual leg of the clip of the self-ligating bracket known from U.S. Pat. No. 5,906,486 A.

The labial surface, which delimits the second slot, is removed or interrupted in the area of the gingival wall of the bracket. This leaves room for the tongue which is to be displaced by the lingual leg of the clip. And it provides the further advantage that it will be easier for a tool, for example a scaler, to act on the gingival end of the lingual leg of the clip for displacing it from its closed position to its open position and to follow the gingival end of the lingual leg of the clip, as the tool used for displacing the clip can be moved along the area where the labial surface delimiting the second slot has been removed or interrupted.

Preferably, the labial surface delimiting the second slot is removed or interrupted also in the area of the groove. There is then ample room for the tongue also below the bottom of the first slot, and according to an additional advantage it is then easily possible to act on the lingual leg of the clip, and to press down the tongue, through the groove from the labial direction. At the same time, that feature reduces friction between the bottom of the first slot and an arch wire in the first slot.

According to an advantageous further development of the intention, the lingual surface, which delimits the second slot, projects beyond the tip of the lingual leg of the clip in any position of the clip, and a positioning aid for a tool is provided at the gingival end and/or before the gingival end of the lingual leg of the clip, by means of which the clip can be displaced from the closed position to the open position by pressure exerted on the gingival end of its lingual leg. This greatly facilitates transfer of the clip from its closed position to its open position the latter being definitely reached when the tongue hits against the occlusal wall.

The described further development provides substantial additional advantages:

- No hole in the labial leg of the clip is needed for displacing the clip from its closed position to its open position. This considerably reduces the risk of food particles being pushed into the area between the clip and the bracket, and being compacted in this space, compared with the prior art.
- Oral hygiene is improved.
- As there is no hole in the labial leg of the clip, the latter is felt much less as a nuisance and looks more attractive.
- Although the position of the gingival end of the lingual leg of the clip is visible in the mouth either not at all or only with difficulty, the clip may easily be displaced from the closed position to the open position by exerting pressure on the gingival end of its lingual leg the point at the gingival end of the lingual leg of the clip, where the pressure is to be applied, can be felt and found even blind using the positioning aid.
- Contrary to the hole in the labial leg of the clip provided according to the invention, the positioning aid provided on the gingival end or in the vicinity of the gingival end of the lingual leg of the clip does not weaken the clip and its restoring force.
- The lingual leg of the clip cannot evade the pressure exerted on its gingival end because it is guided straight in the second slot in which it is fitted. This would be different for pressure acting on the labial leg of the clip, as in this case the clip might be damaged, or the tool may slip off and may injure the patient.
- It is not necessary to procure a special tool for displacing the clip to its open position. Suitable tools are available in any orthodontic practice in great number, for example in the form of scalers.
- The positioning aid reduces the risk of the tool slipping off the gingival end of the lingual leg of the clip when pressure is applied on the gingival end.

A suitable positioning aid may consist of a notch in the gingival end of the lingual leg of the clip. The notch does not weaken the restoring force of the clip and is easy to clean. It can be found by moving the tip of a tool, for example the tip of a scaler, across the base of the bracket, along the edge of the support. One then automatically hits upon that section of the base that projects beyond the tip of the lingual leg of the clip, up to which the lingual surface of the second slot extends. The tool then hits upon the end of the lingual leg of the clip, with its tip automatically entering the notch, so that it can then exert the pressure necessary for displacing the clip from its closed position to its open position.

According to another possibility, a positioning aid consists in a groove, extending in the gingival-to-occlusal direction, in that section of the lingual surface delimiting the second slot that projects beyond the clip. Again, this groove will be necessarily found when the tip of a tool is moved across the base of the bracket along the edge of the support. The fact that the groove has been reached is easily felt. Once the tool is in the groove it can easily be moved in the groove up to the gingival end of the lingual leg of the clip, for displacing the clip to its open position.

The two possibilities may also be combined. Both possibilities are based on the idea to provide a recess, that can be felt using a tool, at a point where pressure is to be applied on the gingival end of the lingual end of the clip.

Preferably, the groove gets narrower from its gingival to its occlusal end and leads to the center of the edge on the gingival end of the lingual leg of the clip. This facilitates the process of finding the groove and of centering the tool on the point best suited for displacing the clip. The groove should extend at least up to the lingual leg of the clip in its closed position. Preferably, it extends still further up to a point below the lingual leg of the clip so that the tool can be guided in the groove over the entire length of displacement of the clip from its closed position to its open position. This further development recommends itself especially in cases where no notch is provided on the gingival end of the lingual leg of the clip.

Preferably, the groove ends at a stop which, with the clip in the closed position, comes to lie below the lingual leg of the clip, at a spacing from the tip of the lingual leg of the clip. Preferably, the stop is located at the point where the tip of the lingual leg of the clip lies in the open position of the clip. This ensures that the movement of the tool will automatically be stopped once the open position of the clip is reached because the tool will then hit against the stop. However, instead of being transmitted to the delicate clip, the peak force will be transmitted to the solid bracket in this case while the clip will be protected.

Preferably, the groove extends in the base of the bracket, at least in part. This is favorable with a view to achieving a small overall height of the bracket which in turn improves the wearing comfort in the mouth. To further the small overall height, the bracket preferably is formed as a single piece. In the case of metal brackets according to the prior art the base frequently is made as a separate part and is connected with the support of the bracket by welding in a second step. According to the invention it is, however, preferred to form the bracket as a single piece, especially by metal injection molding (MIM), a method for the powder-metallurgical production of metallic molded parts related to the injection molding process. With the aid of that method, it is possible to simultaneously form alternately oriented undercut projections on the lower surface of the base of the bracket, which when the bracket is glued onto a tooth lead to clearly improved adhesion of the bracket to the tooth compared with conventional brackets where a wire grating is welded to the lower surface of the base of the bracket. The bonding strength that can be achieved with the aid of the undercut projections is higher by approximately 30% than with brackets provided with a wire grating on their bottom surface. As to the configuration of such undercut projections on the lower surface of the base, reference is made to WO 96/09015 A1. The higher bonding strength achievable in this case is of particular advantage in the case of the present invention because in reduces the risk of the bracket being detached from the tooth by the force applied for displacing the clip from its closed position to its open position and by the tool used for this purpose hitting against the bracket.

BRIEF DESCRIPTION OF THE FIGURES

Further features and advantages of the invention can be derived from the description that follows of one preferred embodiment illustrated in the drawing in which.

DETAILED DESCRIPTION OF THE INVENTION

The bracket is provided with a curved base 1 the curvature of which is approximated to the front of a tooth. The bottom surface 2 of the base 1, which forms the lingual side of the bracket, is provided with undercut projections 3 arranged in series. The projections are rhomb-shaped in the cross-section shown in FIGS. 3 and 4, and are rectangular in a cross-section taken in parallel to the bottom surface 2. In order to glue the bracket onto a front of a tooth, an adhesive may be applied on the bottom surface 2. Due to the interleaving between the projections 3 and the adhesive good bonding strength is achieved. The projections 3 and, together with them, the undercuts are equally orientated in each row. Between the rows they are, however, alternately oriented in one and the other direction. This has the effect that when a force is applied on the bracket in the gingival-to-occlusal direction the same bonding strength will be achieved as in the case of a force acting in the occlusal-to-gingival direction.

Figure 1:
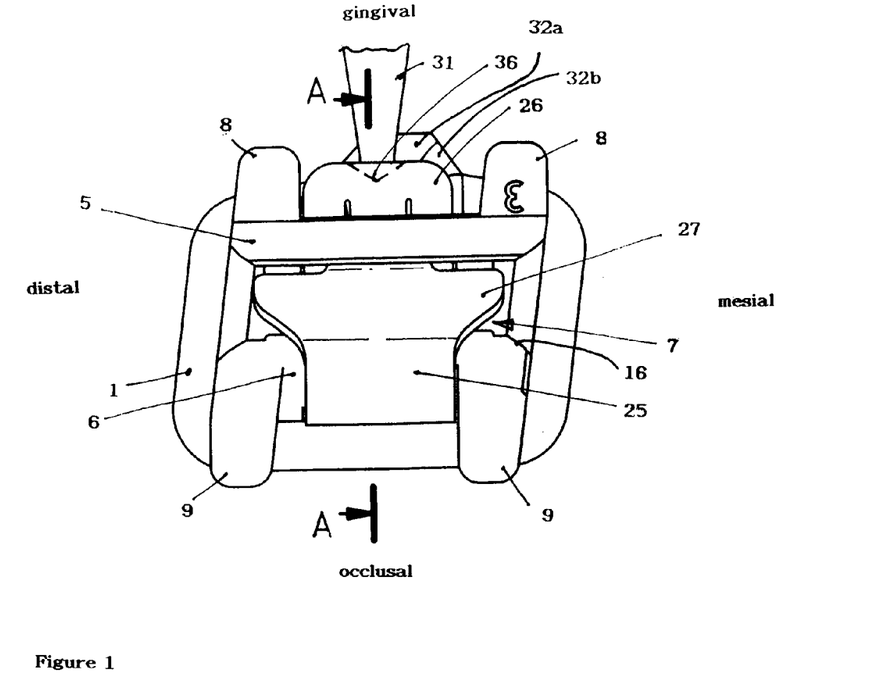
FIG. 1 shows a top view of a bracket according to the invention with the bracket in its closed position.
Figure 2:
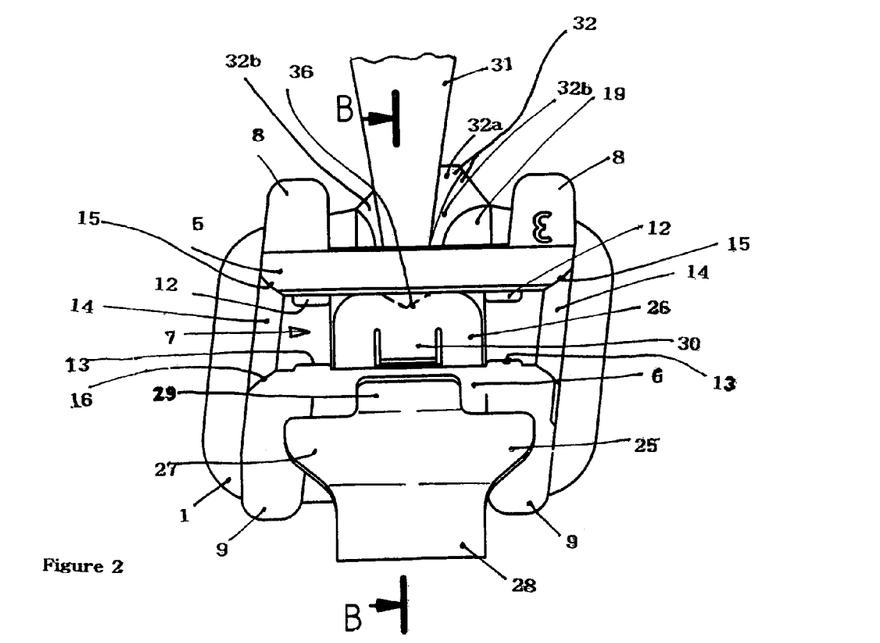
FIG. 2 shows a top view of the bracket with the clip in its open position.

FIG. 1 shows the orientation on a tooth envisaged for a bracket with respect to the gingival-to-occlusal and the distal-to-mesial directions.

The base 1 transitions to a support 4 which carries a gingival wall 5 and an occlusal wall 6. The two walls 5 and 6 extend in parallel one to the other and are separated by a first slot 7 which extends continuously along a straight line from distal to mesial and which is open in the labial direction.

Two ligature wings 8 projecting in the gingival direction are provided on the gingival wall 5. Two ligature wings 9 projecting in the occlusal direction are provided on the occlusal wall 6. These wings serve for attaching ligature wires in a manner known to the man of the art.

Figure 4:
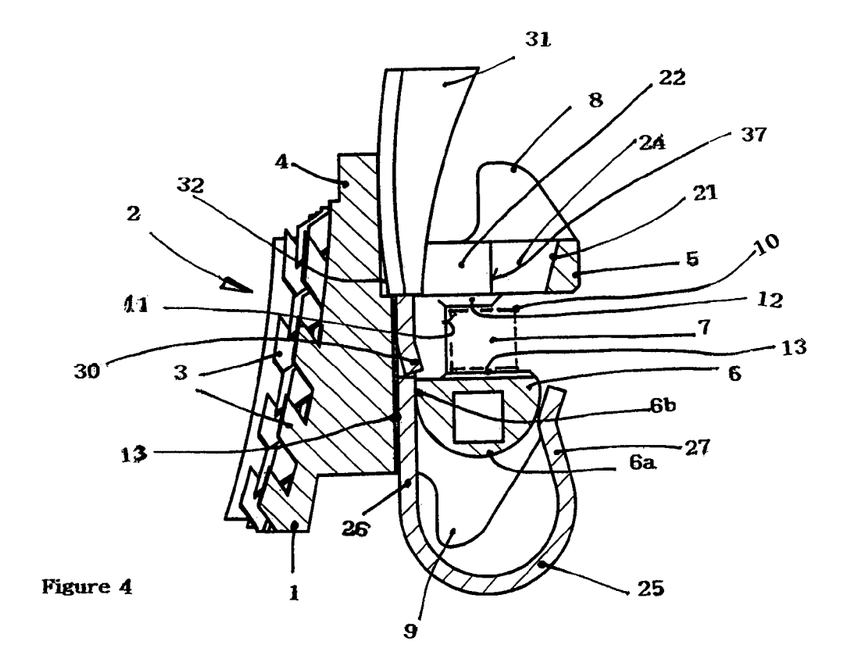
FIG. 4 shows a cross-section of the bracket along line B-B in FIG. 2.
Figure 5:
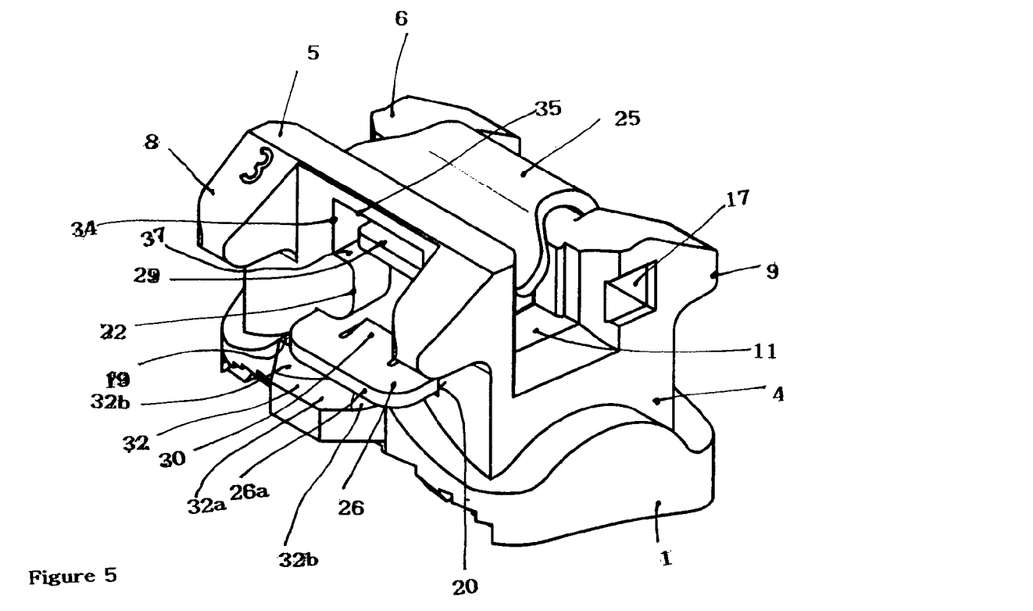
FIG. 5 shows an oblique view of the gingival and labial side of the bracket according to FIGS. 1 and 3.
Figure 6:
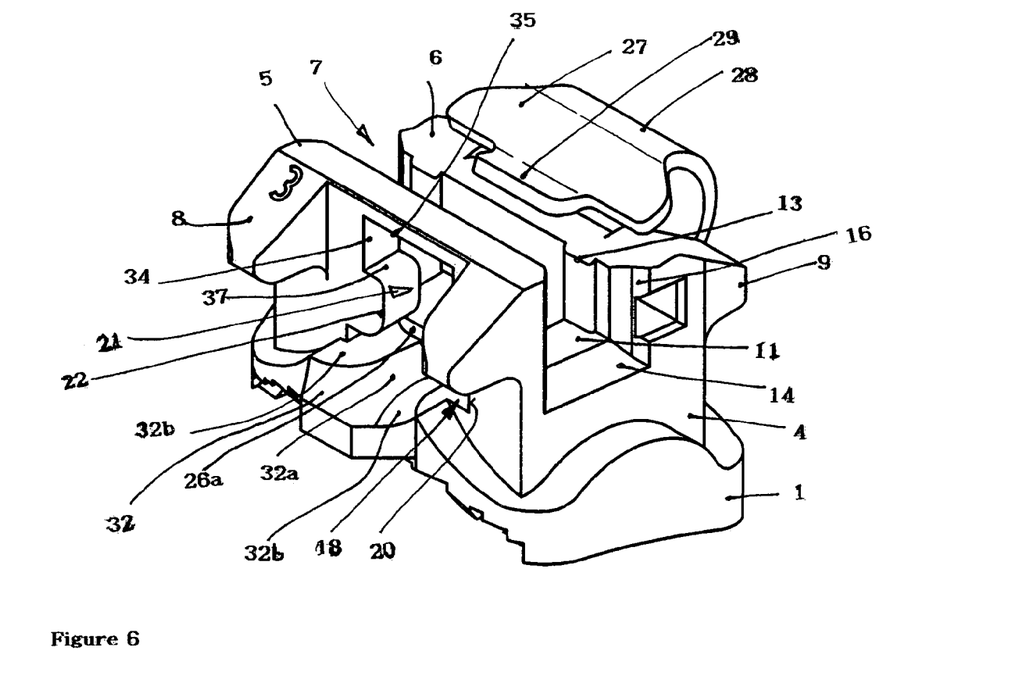
FIG. 6 shows an oblique view of the gingival and labial side of the bracket according to FIGS. 2 and 4.
Figure 7:
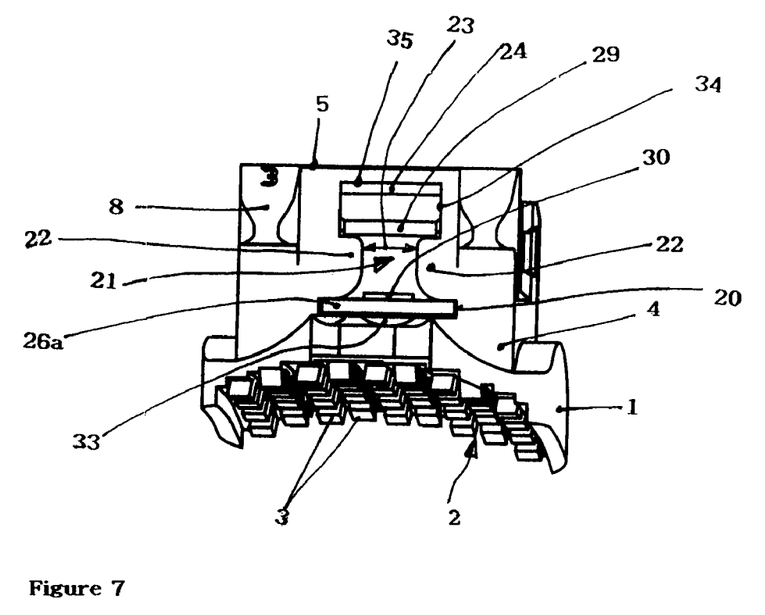
FIG. 7 shows an oblique view of the gingival and labial side of the bracket according to FIG. 5.
Figure 8:
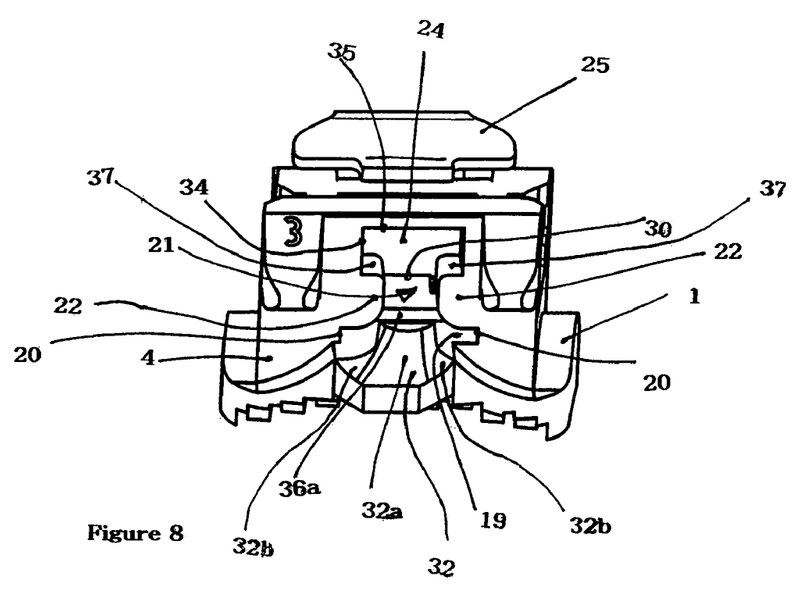
FIG. 8 shows an oblique view of the gingival and labial side of the bracket, viewed from the gingival side, with the bracket in its open position.

The first slot 7 serves to receive an arch wire 10 which, specifically, has a rectangular cross-section and which is not part of the bracket and, therefore, is indicated in FIG. 4 only by broken lines. By pre-stressing the arch wire 10, a pressure can be applied on the bottom 11 of the first slot 7 and a torque can be applied on the walls 5 and 6 of the bracket. To this end, the clear cross-section of the first slot 7 has a substantially rectangular shape. In the present case, it is delimited by the bottom 11 of the first slot 7 and by ribs 12 on the gingival wall 5 and by ribs 13 on the occlusal wall 6, which serve to reduce friction of the arch wire 10 in the first slot 7. As will be described in more detail further below, the bottom 11 of the first slot 7 does not extend at the same level over the full length of the first slot 7, but is interrupted. This likewise reduces friction of the arch wire 10 in the first slot 7. At the ends of the first slot 7, there are provided rounded oblique surfaces 14 on the bottom of the groove, rounded oblique surfaces 15 on the gingival wall 5 and rounded oblique surfaces 16 on the occlusal wall 6 that serve to increase the inlet to the first slot 7 and further to reduce the friction encountered by the arch wire 10 in the first slot 7; this is especially advantageous in the case of heavy misalignments of the teeth where the arch wire necessarily will assume an especially irregular shape.

In the occlusal wall 6, there is provided a channel 17 extending continuously from distal to mesial for receiving some accessory element, such as a spring, a small hook or an accessory wire.

A second slot 18, delimited on its lingual side by a flat surface 19 extending in parallel to the bottom 11 of the first slot 7, extends below the bottom 11 of the first slot 7 in parallel to the bottom 11 of the first slot 7. That surface 19 starts at the occlusal wall 6 and extends crosswise through the bracket, and runs initially through the support 4 and finally through the gingival portion of the bracket in its base 1. In the vicinity of the ligature wings 8 and 9, the second slot 18 is delimited by narrow side walls 20 extending in parallel one to the other and at a right angle to the lingual surface 19. Above the second slot 18, the occlusal wall 6 is provided, on its side facing away from the first slot 7, with a surface 6a in the form of a cylinder envelope, which transitions in the area of the second slot 18 into a flat surface 6b, extending in parallel to the lingual surface 19 and arranged on the labial side of the second slot 18. This provides a funnel-like inlet to the second slot 18 on the occlusal side of the bracket. Between the side walls 20, the bottom of the first slot 7 is lowered to the lingual surface 19 of the second slot 18.

In the gingival wall 5, there is provided a window 21 which is bordered by the lingual surface 19, the side walls 20 and oppositely directed projections 22 following the side walls 20, between which an interruption 23 exists in the gingival wall 5, by two edges 34 extending in parallel to the side walls 20 and by a labial edge 35. The lingual edges of the projections 22 are aligned with the labial surface 6b of the second slot 18 in the occlusal wall 6 and serve, just as the labial surface 6b, as guides for the lingual leg of the clip 25. The edges 34 and 35, as well as the projections 22, being elements of the window 21, define a substantially rectangular cutout 24, which has a length, measured in the distal-to-mesial direction, greater than the spacing between the projections 22, but smaller than the spacing between the gingival ligature wings 8, and also smaller than the spacing between the ribs 12 and 13, which in the present case is identical to the spacing between the side walls 20. The ribs 12 provided on the gingival wall 5 end at the level of the lingual edge of the rectangular cutout 24, being simultaneously the labial edge of the projections 22.

The bracket comprises a clip 25 made from a spring material. The bracket has a straight lingual leg 26 and, compared with the latter, a shorter labial leg 27 of approximately straight shape. The two legs 26 and 27 are connected by an occlusal section 28 having approximately the shape of an arc of a circle. That section has the same width as the lingual section 26, which fits into the second slot 18 with little play. The labial leg 27 widens to approximately the length of the first slot 7. It does not extend in parallel, but rather at an acute angle to the lingual leg 26 and approaches the latter on its way from the occlusal section 28. The labial leg 27 is provided on its gingival end with an extension 29, extending in the gingival direction, which is angled in the labial direction. The extension 29 is narrower than the labial leg 27 and narrower than the lingual leg 26; it fits with little play into the cutout 24, which is part of the window 21 in the gingival wall 5.

A tongue 30 is cut out from the lingual leg 26, in the vicinity of its gingival end 26a, and is raised at an acute angle relative to the lingual leg 26, in a direction toward the occlusal section 28.

The clip 25 is connected with the bracket by inserting the lingual leg 26, coming from the occlusal direction, into the second slot 18. During this process, the tongue 30 is progressively urged through the narrowing inlet of the second slot 18 and into the cutout of the lingual leg 26 from which it has been cut out. Once the tongue 30 has passed the occlusal wall 6 it will spring back and will then be directed against the occlusal wall 6 with the result that it can no longer get lost. As the clip 25 is advanced to this position, the extension 29 will hit upon the surface 6a of the occlusal wall 6, having the form of a cylinder envelope, and will slide along that wall up to its labial surface, whereby the clip 25 will be expanded against the action of its elastic restoring force. As the clip 25 is further advanced, the labial leg 27 of the clip 25 will slide off the labial surface of the occlusal wall 6 and will spring into the first slot 7 where it may contact an arch wire 10. The springing-back action of the clip 25 has the effect to further advance the spring because the spring will be pushed back by the occlusal wall 6 until its extension 29 will engage the cutout 24. One thereby secures the arch wire 10 in the first slot 7 as the arch wire 10 cannot lift the labial leg 27 of the clip beyond the point where its extension 29 hits against the labial edge of the cutout 24. The lingual edges 37 of the cutout 24 are simultaneously the labial edges of the projections 22; they determine the smallest spacing between the labial leg 27 of the clip 25 and the bottom 11 of the first slot 7. This provides the advantage that thinner arch wires lying in the first slot 7, that do not reach the lingual edge 37, will not be exposed to the clamping effect of the clip 25. Such thinner arch wires are often used at the beginning of a treatment for correction of the tooth position and accelerate the correction process provided they are not pinched. Thicker arch wires 10 are in resilient contact with the labial leg 27. In order to reduce friction between the arch wire 10 and the clip 25, the distal and the mesial edges of the labial leg 27 are preferably rounded or provided with an oblique surface.

Figure 3:
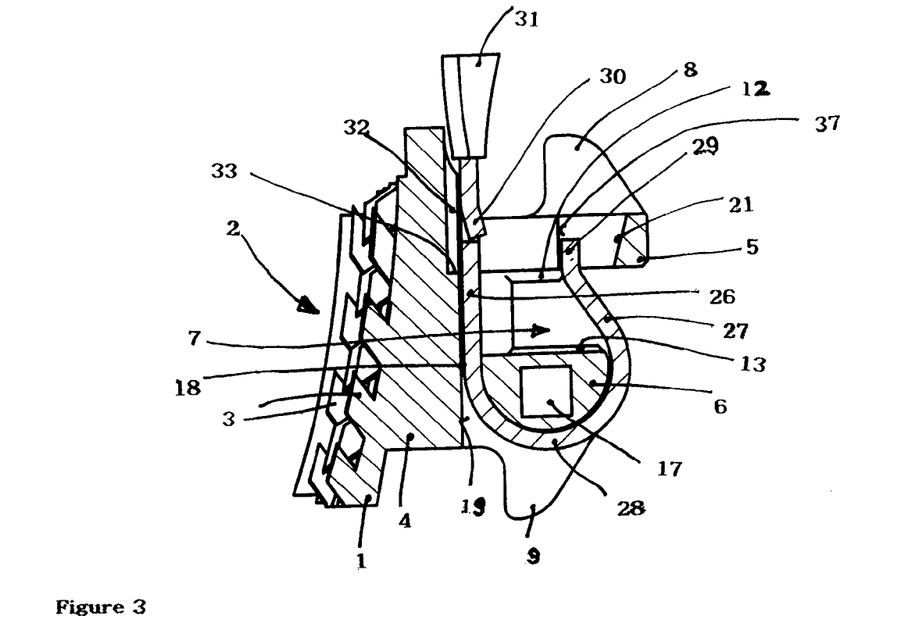
FIG. 3 shows a cross-section of the bracket along line A-A in FIG. 1.
Figure 9:
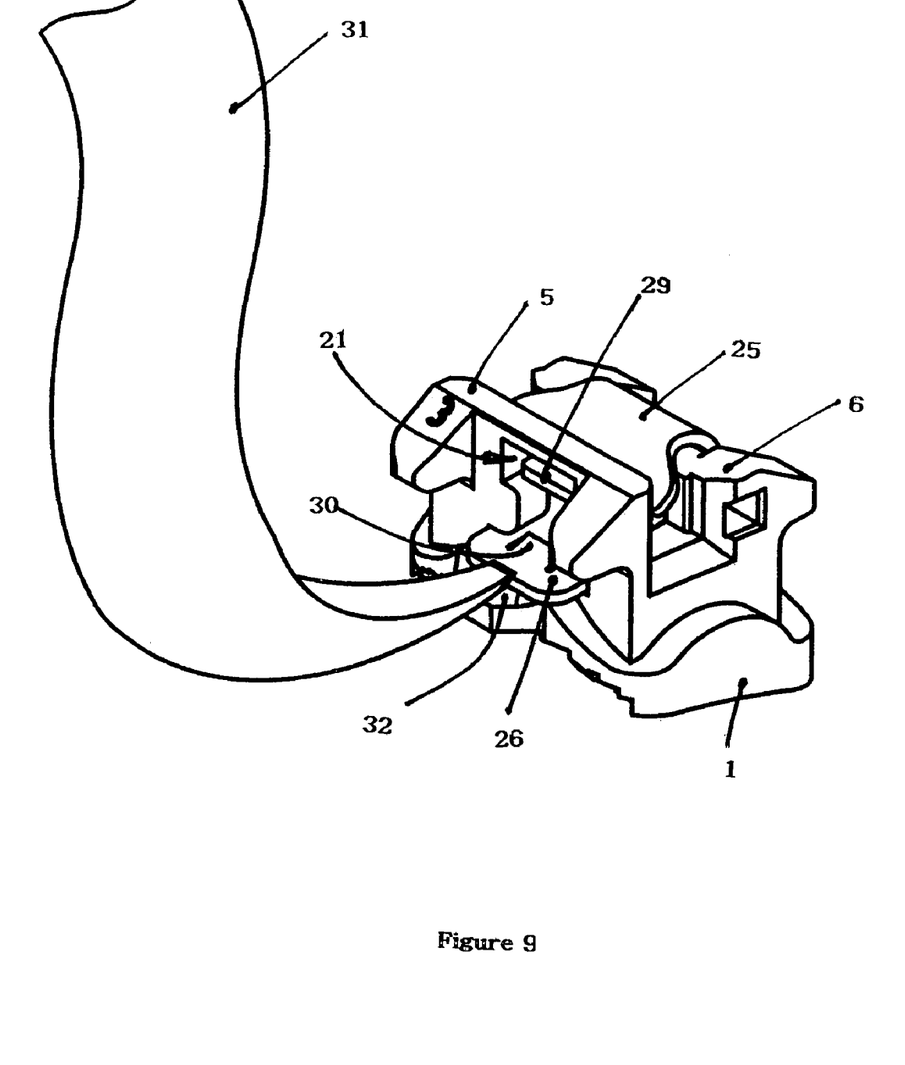
FIG. 9 shows a view of the bracket similar to that of FIG. 5, with a scaler applied.
Figure 10:
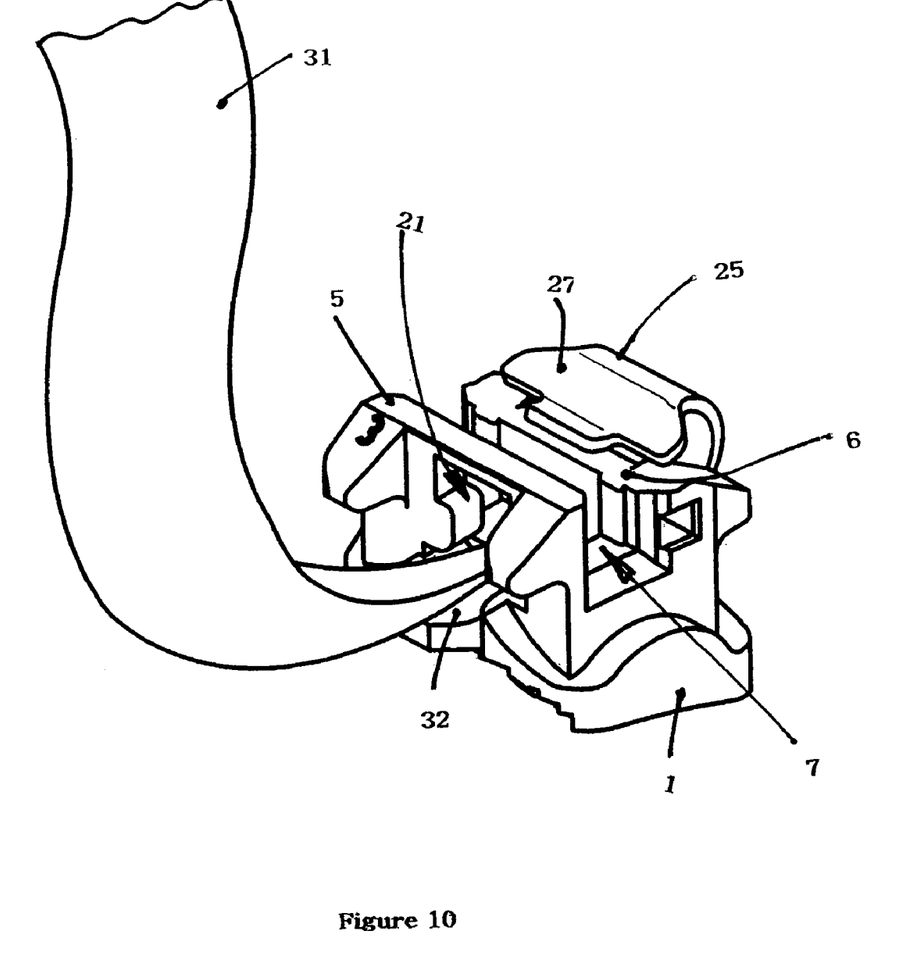
FIG. 10 shows a view of the bracket similar to that of FIG. 6, with a scaler applied.
Figure 11:
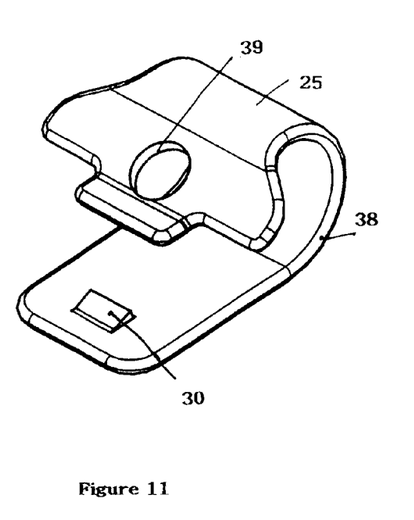
FIG. 11 is a perspective view of a modified clip for use in a bracket of the type shown in FIGS. 1 to 10.
Figure 12:
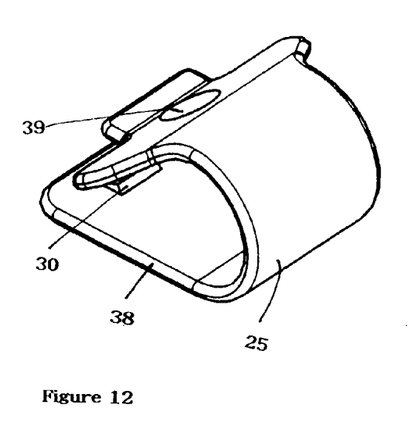
FIG. 12 is another perspective view of the clip shown in FIG. 11.
Figure 13:
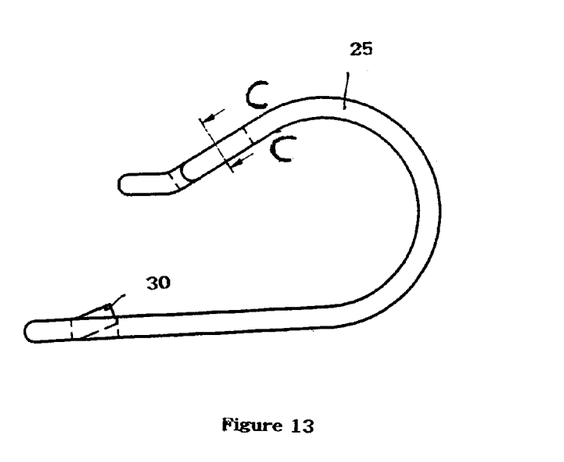
FIG. 13 is a side elevational view of the clip shown in FIG. 11.
Figure 14:
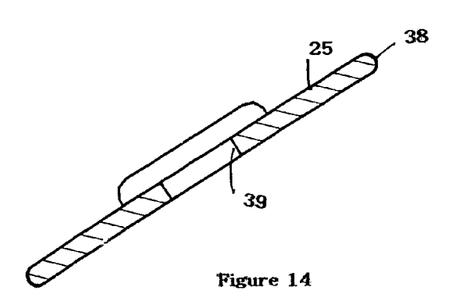
FIG. 14 is a sectional view C-C of the clip according to FIG. 13.

For transferring the clip 25 from its closed position (FIG. 1, FIG. 3, FIG. 5, FIG. 9) to its open position (FIG. 2, FIG. 4, FIG. 6, FIG. 10), one takes a tool 31, for example a scaler, and applies it to the gingival edge of the lingual leg 26, as illustrated in FIGS. 1, 3 and 9. One can feel this point, without having to see it, because a surface 19, which delimits the second slot 18 on its lingual side, extends in the gingival direction so far that it projects beyond the gingival end of the lingual leg 26 of the clip 25. Further, a groove 32 provided in the lingual surface 19 starts out from the gingival end of that surface and extends to a point below the lingual leg 26. That groove 32 has an approximately flat central portion 32a, flanked by two concave sections 32b, which provide a transition between the central section 32a and the lingual surface 19. The groove 32 narrows in the gingival-to-occlusal direction and ends at a stop 33. The groove 32 serves a positioning aid for the tool 31, serving to feel the groove 23. Once the groove 32 has been found, the clip 25 is displaced in the gingival-to-occlusal direction using the tip of the tool, the tip of the tool 31 being further guided in the correct direction by the groove 32. The displacing movement ends when the tool 31 hits against the stop 33. The stop 33 is located so that the tongue 30 will occupy a position a short way before the occlusal wall 6, indicated in FIG. 4, when the tool 31 hits upon the stop 33 during displacement of the clip 25. The clip 25 then is in its open position. In this open position, the labial leg 27 of the clip is in its rest position on the occlusal wall 6, in which it frees the access to the first slot 7 from the labial direction.

Even if the stop 33 should be overcome by the tool 31, the clip 20 can be displaced in the occlusal direction only until the tongue 30 hits against the occlusal wall 6. Thus, the clip 25 cannot get lost during transfer from its closed position (FIG. 3) to its open position (FIG. 4). For separating the clip 25 completely from the bracket, it is necessary to urge the tongue 30 back into the recess from which is has been cut out using a tool, and to push or pull the clip 25 a further distance in the occlusal direction with the tongue 30 in pressed-down condition.

A notch 36, indicated in the drawings by broken lines only, may be provided centrally on the gingival edge of the lingual leg 26 of the clip 25. That notch may serve as a positioning aid instead of, or in addition to, the groove 32.

FIGS. 11 to 14 show a modified clip 25, which differs from the clip 25 according to FIGS. 1 to 10 in that its total edge 38 is rounded. The rounded edge 38 is particularly advantageous in the area of the first slot 7 because it enables the arch wire 10 to move with lower friction in the first slot 7. A hole 39 is provided to insert a tool for moving the clip 25 on the bracket.

The invention claimed is:

1. Self-ligating bracket for use in orthodontics comprising
a base;
a support arranged on the base
an occlusal wall with at least one occlusal ligature wing extending from the support;
a gingival wall with at least one gingival ligature wing extending from the support;
a first slot separating the occlusal wall and the gingival wall one from the other and extending continuously in the mesial-to-distal direction;
a second slot which extends continuously through the support in the gingival-to-occlusal direction, and which is limited by a lingual surface and by a labial surface; and
a resilient clip having a labial leg and a lingual leg that are connected one to the other by an occlusal section;
the lingual leg being received in the second slot and being arranged for displacement in the second slot in the gingival-to-occlusal direction between a closed position in which the labial leg extends into a recess in the gingival wall and an open position of the clip in which the tip of the labial leg rests on the occlusal wall,
wherein a tongue, directed toward the occlusal wall, is cut out from the lingual leg of the clip and is bent off in the labial direction so that an acute angle is enclosed between the tongue and the lingual leg of the clip, wherein the labial surface, which delimits the second slot, is removed or interrupted in the area of the gingival wall.

2. The bracket as defined in claim 1, wherein the angle between the lingual leg of the clip and the tongue is between 15° and 25°.

3. The bracket as defined in claim 1, wherein it is formed as a single piece.

4. The bracket as defined in claim 1, wherein the labial leg of the clip is provided with an oblique surface and/or a rounded surface on its distal edge and its mesial edge.

5. The bracket as defined in claim 1, wherein the first slot is provided with oblique surfaces and/or rounded surfaces on its distal end and on its mesial end.

6. The bracket as defined in claim 1, wherein two ribs each are provided in the first slot on the gingival wall and on the occlusal wall, which ribs extend in the occlusal-to-gingival direction.

7. The bracket as defined in claim 6 in which the ribs have chamfered or rounded edges.

8. The bracket as defined in claim 1, wherein the clip has a rounded edge.

9. The bracket as defined in claim 8, wherein the total edge of the clip is rounded.

10. Self-ligating bracket for use in orthodontics comprising
a base;
a support arranged on the base;
an occlusal wall with at least one occlusal ligature wing extending from the support;
a gingival wall with at least one gingival ligature wing extending from the support;
a first slot separating the occlusal wall and the gingival wall one from the other and extending continuously in the mesial-to-distal direction;
a second slot which extends continuously through the support in the gingival-to-occlusal direction, and which is limited by a lingual surface and by a labial surface; and
a resilient clip having a labial leg and a lingual leg that are connected one to the other by an occlusal section;
the lingual leg being received in the second slot and being arranged for displacement in the second slot in the gingival-to-occlusal direction between a closed position in which the labial leg extends into a recess in the gingival wall and an open position of the clip in which the tip of the labial leg rests on the occlusal wall,
wherein a tongue, directed toward the occlusal wall, is cut out from the lingual leg of the clip and is bent off in the labial direction so that an acute angle is enclosed between the tongue and the lingual leg of the clip, wherein the labial surface delimiting the second slot is removed or interrupted in the area of the first slot.

11. The bracket as defined in claim 10 wherein the angle between the lingual leg of the clip and the tongue is between 15° and 25°.

12. The bracket as defined in claim 10, wherein it is formed as a single piece.

13. The bracket as defined in claim 10, wherein the labial leg of the clip is provided with an oblique surface and/or a rounded surface on its distal edge and its mesial edge.

14. The bracket as defined in claim 10, wherein the first slot is provided with oblique surfaces and/or rounded surfaces on its distal end and on its mesial end.

15. The bracket as defined in claim 10, wherein two ribs each are provided in the first slot on the gingival wall and on the occlusal wall, which ribs extend in the occlusal-to-gingival direction.

16. The bracket as defined in claim 15 in which the ribs have chamfered or rounded edges.

17. The bracket as defined in claim 10, wherein the clip has a rounded edge.

18. The bracket as defined in claim 17, wherein the total edge of the clip is rounded.

19. Self-ligating bracket for use in orthodontics comprising
a base;
a support arranged on the base
an occlusal wall with at least one occlusal ligature wing extending from the support;
a gingival wall with at least one gingival ligature wing extending from the support;
a first slot separating the occlusal wall and the gingival wall one from the other and extending continuously in the mesial-to-distal direction;
a second slot which extends continuously through the support in the gingival-to-occlusal direction, and which is limited by a lingual surface and by a labial surface; and
a resilient clip having a labial leg and a lingual leg that are connected one to the other by an occlusal section;
the lingual leg being received in the second slot and being arranged for displacement in the second slot in the gingival-to-occlusal direction between a closed position in which the labial leg extends into a recess in the gingival wall and an open position of the clip in which the tip of the labial leg rests on the occlusal wall,
wherein a tongue, directed toward the occlusal wall, is cut out from the lingual leg of the clip and is bent off in the labial direction so that an acute angle is enclosed between the tongue and the lingual leg of the clip, wherein the lingual surface, which delimits the second slot, projects beyond the tip of the lingual leg of the clip in any position of the clip, and that a positioning aid for a tool is provided on the gingival end and/or before the gingival end of the lingual leg of the clip, by means of which the clip can be displaced from the closed position to the open position by pressure exerted on the gingival end of its lingual leg.

20. The bracket as defined in claim 19, wherein the positioning aid is formed by a groove provided in the base and extending from gingival to occlusal, wherein the groove ends at a stop which occupies a position below the lingual leg of the clip at a spacing from the tip of the lingual leg of the clip when the clip is in its closed position.

21. The bracket as defined in claim 20, wherein the stop comes to lie approximately in the area where the tip of the lingual leg of the clip finds itself in the open position of the clip.

22. The bracket as defined in claim 20, wherein the stop still lies below the lingual leg of the clip in the position of the clip in which the tongue hits against the occlusal wall.

23. The bracket as defined in claim 20, wherein the tongue hits against the occlusal wall in the open position of the clip.

24. The bracket as defined in claim 19, wherein a notch is provided as positioning aid in the gingival end of the lingual leg of the clip.

25. The bracket as defined in claim 19, wherein a groove, which extends in the gingival-to-occlusal direction, is provided as positioning aid in the projecting section of the lingual surface that delimits the second slot.

26. The bracket as defined in claim 25, wherein the groove extends below the lingual leg of the clip in its closed position.

27. The bracket as defined in claim 25, wherein the groove gets narrower from its gingival to its occlusal end.

28. The bracket as defined in claim 25, wherein the groove extends in the base at least in part.

29. The bracket as defined in claim 19 wherein the angle between the lingual leg of the clip and the tongue is between 15° and 25°.

30. The bracket as defined in claim 19, wherein it is formed as a single piece.

31. The bracket as defined in claim 19, wherein the labial leg of the clip is provided with an oblique surface and/or a rounded surface on its distal edge and its mesial edge.

32. The bracket as defined in claim 19, wherein the first slot is provided with oblique surfaces and/or rounded surfaces on its distal end and on its mesial end.

33. The bracket as defined in claim 19, wherein two ribs each are provided in the first slot on the gingival wall and on the occlusal wall, which ribs extend in the occlusal-to-gingival direction.

34. The bracket as defined in claim 33 in which the ribs have chamfered or rounded edges.

35. The bracket as defined in claim 19, wherein the clip has a rounded edge.

36. The bracket as defined in claim 35, wherein the total edge of the clip is rounded.

* * * * *